United States Patent [19]
Lemelson et al.

[11] Patent Number: 5,878,746
[45] Date of Patent: Mar. 9, 1999

[54] COMPUTERIZED MEDICAL DIAGNOSTIC SYSTEM

[76] Inventors: Jerome H. Lemelson, Suite 286, Unit 802 930 Tahoe Blvd., Incline Village, Nev. 89451-9436; J. Kevin Parker, 551 Green Bay Rd., Highland Park, Ill. 60035

[21] Appl. No.: 465,954

[22] Filed: Jun. 6, 1995

[51] Int. Cl.$^6$ ....................................................... A61B 5/00
[52] U.S. Cl. ........................ 128/653.1; 128/920; 128/922; 382/190; 395/10; 395/924
[58] Field of Search ................... 128/653.1; 364/413.02, 364/413.13, 413.22; 382/108, 189, 190, 195, 203; 395/10, 52, 924

[56] References Cited

U.S. PATENT DOCUMENTS

4,839,822 6/1989 Dormond et al. .
5,133,020 7/1992 Giger et al. .
5,235,510 8/1993 Yamada et al. .
5,437,278 8/1995 Wilk .
5,463,548 10/1995 Asada et al. .
5,465,308 11/1995 Hutcheson et al. .

*Primary Examiner*—Scott M. Getzow
*Assistant Examiner*—Shawna J Shaw

[57] ABSTRACT

A computerized system is disclosed for performing various medical diagnostic tests and evaluating the results thereof. In one form, image data generated from an imaging device, such as a CAT, PET, or MRI scanner, is analyzed by computer and compared with coded information defining past images of the same patient and/or standard images in order to assess the patient's condition. The system may incorporate various types of both imaging and non-imaging modalities for providing data inputs which are stored in a database for analysis. In one particular embodiment, a computer automatically controls the performance of certain tests in accordance with its evaluation of the current input data.

23 Claims, 4 Drawing Sheets

COMPUTERIZED MEDICAL DIAGNOSTIC SYSTEM

BACKGROUND AND SUMMARY OF THE INVENTION

Modern medical technology has produced a plethora of diagnostic testing modalities which are useful in diagnosing and evaluating disease. The amount of potentially useful data which can be generated from such testing modalities, including both image and non-image data, is enormous. However, because it is prohibitively expensive to perform every test which would yield useful information in evaluating a particular patient, physicians must balance the cost of a test versus its potential benefit before deciding that it should be performed. One factor causing such expense is the capital cost of the testing equipment, which is amortized and then reflected in the fee charged for each test. Another factor is the cost of the labor required of health care providers in both performing and evaluating diagnostic testing. It is toward the goal of reducing the costs caused by the latter factor that the present invention is directed.

The present invention is a system and method whereby medical examinations and evaluations of body fluids, tissues, structure, appearance, etc. may be automatically made, recorded and/or compared to past records of such examinations for the purpose of diagnosis and early treatment of disease. This system is designed to make use of artificial intelligence for accurate and rapid diagnosis and for adaptability. In one form, a digital computer is programmed to analyze clinical data according to criteria contained in a knowledge database in order to make both diagnoses and recommendations for further testing. A system and method in accordance with the invention incorporates a plurality of data input devices for directly inputting image and non-image data into the system for evaluation as well as allowing the manual inputting of other relevant clinical parameters. In a particular embodiment, the data input devices are under computer control so that certain tests may be performed automatically in accordance with the computer's evaluation of the input data.

It is a primary object of the present invention to provide a computerized system for diagnosing disease whereby clinical data pertaining to a particular patient is collected and automatically compared with previously collected data.

Another object is to provide a system and method for automatically making recommendations for further diagnostic testing based on present and past input data Another object is to provide a system and method whereby imaging and non-imaging diagnostic devices are automatically operated by a computer which is programmed to evaluate data from the diagnostic devices as it is generated.

DETAILED DESCRIPTION OF THE INVENTION

Figure 1:
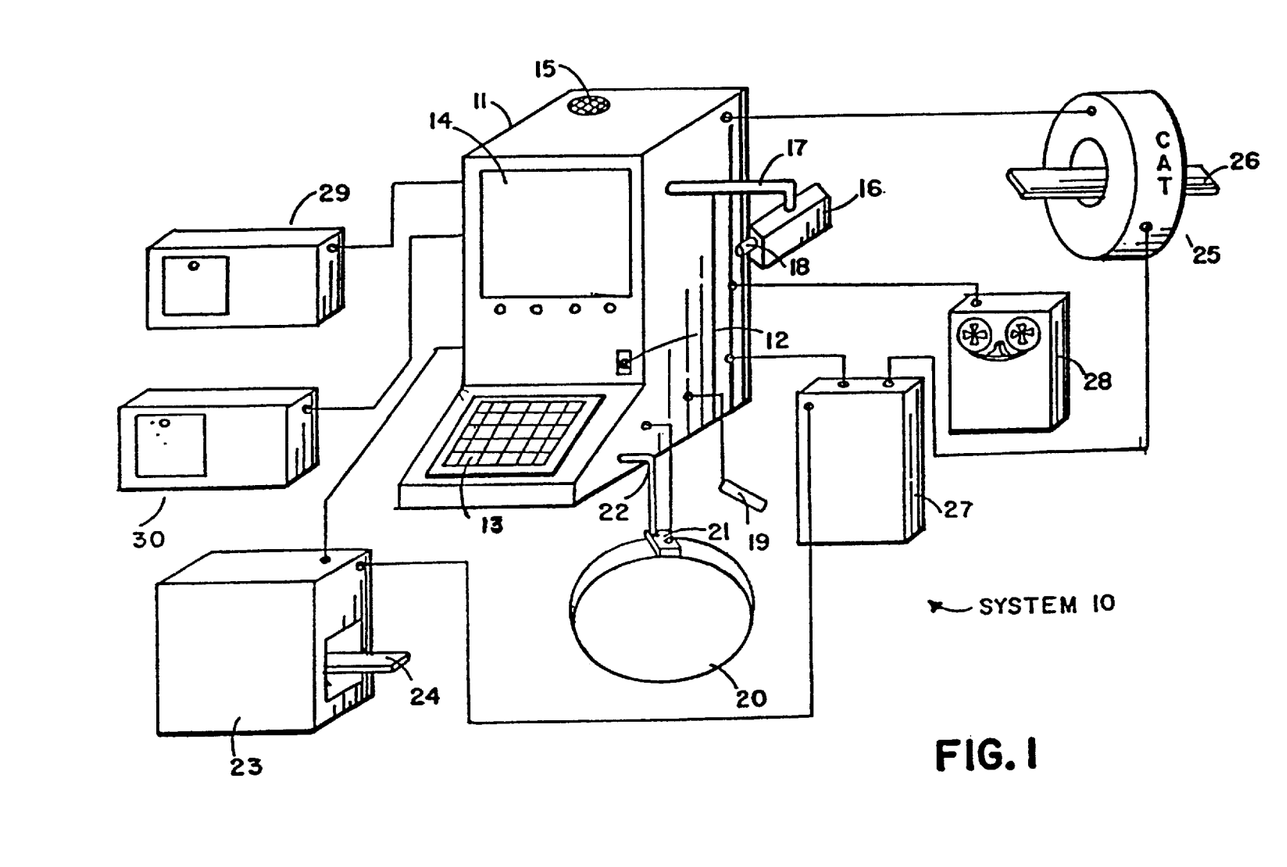
FIG. 1 shows the physical arrangement of a medical diagnostic system in accordance with the present invention.

FIG. 1 shows the arrangement of an exemplary computerized medical diagnostic system 10. Shown supported by a housing 11 is on/off switching means 12, a data entry keyboard 13, a data display monitor 14, environmental air intake port 15, and a television camera 16, its focusing lens 18, and an adjustable support arm 17 on which the camera is mounted.

Illustrated as connected to the contents of housing 11 are: an electronic body temperature thermometer 19, an automatically operated blood pressure cuff 20 with its blood pressure sensor 21 and inflation gas conduction tube 22 (such devices are known in the art), an electronic thermography scanner 23 with a slide in patient table 24, an ultrasonic or x-ray CAT (computer axial tomography) or MRI scanner 25 which may be connected to and interact directly with a computer 27. CAT scanner has a maneuverable patient table 26. System 10 also involves a large scale memory means 28 (such as a magnetic tape drive), a histological sample analysis station 29, and a hematological or other body fluid analysis station 30.

Figure 2:
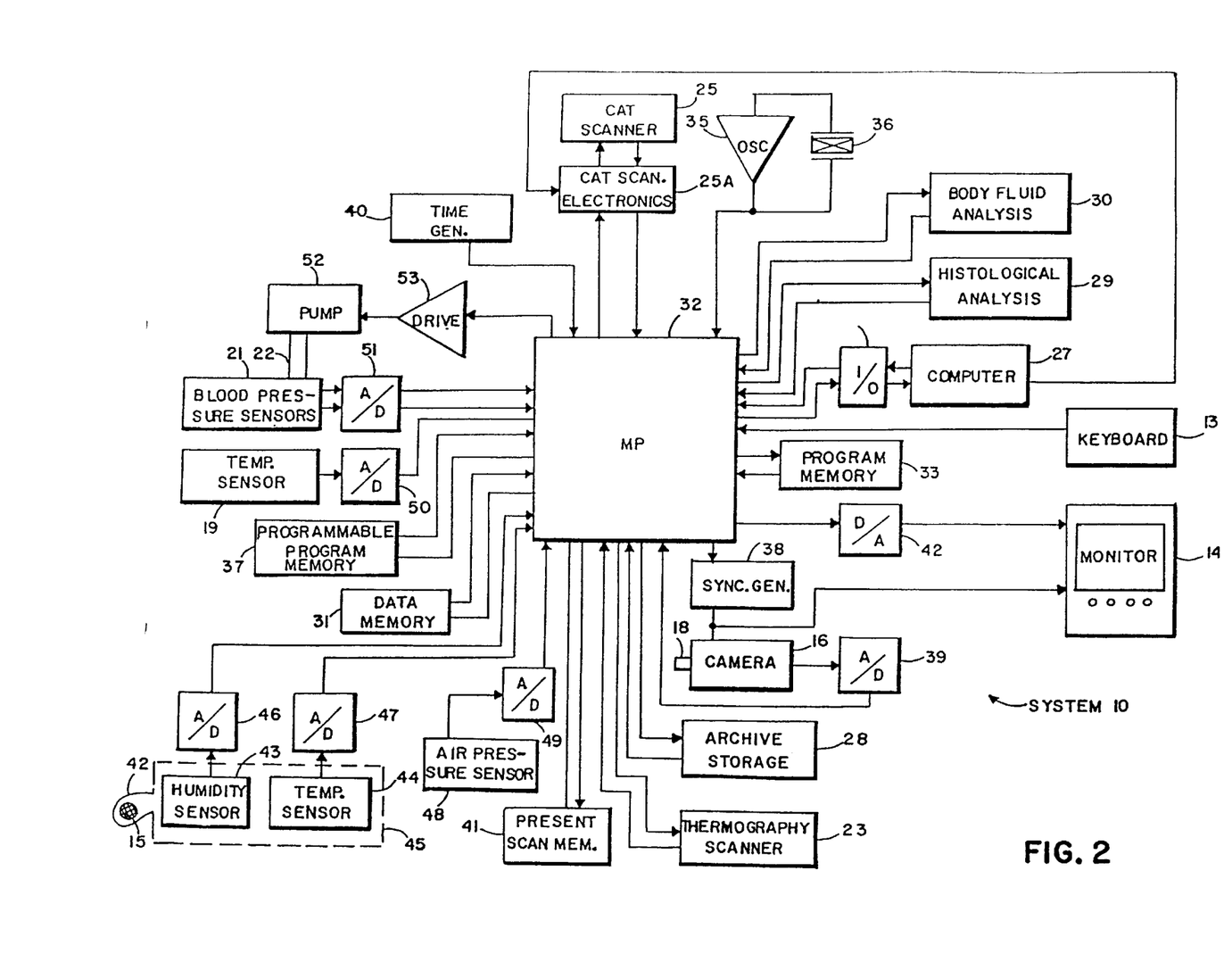
FIG. 2 is a block diagram of the components of the system shown in FIG. 1.

FIG. 2 illustrates the electronic configuration of a typical system 10 in schematic form. A power supply of the appropriate design and parameters with sufficient patient-powerline isolation qualities and with an on/off switching means 12 is assumed to be properly connected to operate the subsystems of system 10 and render them fully functional.

In operation, patient data such as codes defining patient identification, symptoms (if any), tests to be performed, etc. may be entered by an operator into system 10 via digitally encoded keyboard 13. Such patient data is recorded in a programmable data memory means 31 via a microprocessor 32 according to instructions in its program memory means 33. Clock timing signals for the synchronization of other operations of the microprocessor 32 are provided by clock oscillator 35 with its attendant stable accurate feedback means 36 (such as a quartz crystal). Specific and particular programming for the system 10 may also be entered via keyboard 13 for the proper operation of microprocessor 32, and is stored in a programmable program memory means 37 for later retrieval. All microprocessor controlled operations will be hereinafter considered to be in accordance with instructions contained in the program memory 33 or the programmable program memory 37 as modified for the particular patient according to patient data derived from data memory 31.

The system 10 may scan the patient's face, whole body or any select part thereof with the video camera 16 as focused by the computer-controlled lens 18. Synchronization signals for the vertical and horizontal sweep of said camera 16 are provided by a sync generator 38 (which also provides sync input the the monitor 14, a CRT or other type of display terminal). The output of the camera 16 is converted to pixel color and brightness representative digital codes by an A/D converter 39 which codes are conducted therefrom to the microprocessor 32 for recording in the archival memory means 28 along with the patient identification data from the memory 31 and time and date indicating codes generated by a digital time generator 40. Such recorded image information may also be compared with similar previously recorded image information of the patient which previous image information has been retrieved from the archival memory 28 by the microprocessor 32. Such analysis results may be entered as coded data in data memory 31. Also the image signals may be stored (for still-picture freeze frame operation) in a present scan memory 41, such as a RAM or shift register, and may also be immediately displayed on the monitor 14, via microprocessor 32 and the use of a D/A converter 42. Any operating data generated by the system, such as intermediate or final results, or data defining system status, may also be displayed on the monitor 14 under control of the microprocessor 32.

A thermography scanner 23 is interconnected with the microprocessor 32 and provides digital image data based on body heat. Codes defining the present thermography scan are stored in memory and may be compared to codes defining past scans as stored in the archival memory 28. The results of such analysis are recorded in data memory 31. The past and present scan results may also be displayed on the screen of monitor 14. The digital image data produced by the CAT scanner 25 and associated electronics 25A may be recorded in the archival memory 28 and the present scan memory 41 and/or compared to past CAT scan data for analysis under control of the microprocessor 32 with the results of said analysis being stored in data memory 31. The CAT scan image may also be displayed on the monitor 14. Other types of imaging modalities, which may supplement or replace CAT scanning in system 10, include ultrasonography and magnetic resonance imaging.

Environmental parameters may also be sensed, recorded and used in computerized automatic diagnosis analysis at the time of the examination. For this purpose a forced air blower 42 with an outside air intake 15 causes a constant supply of fresh room air to be passed over the humidity sensor 43, such as a hygristor, and a temperature sensor 44, such as a thermistor, both contained within the air duct 45, indicated by a dashed line. Such sensors 43 and 44 provide signals proportional to their respective environmental parameters, which analog signals are converted to representative digital codes by respective A/D converters 46 and 47 and are conducted to the microprocessor 32 for use in analyses and recording. Air pressure may similarly be utilized and is sensed by an air pressure sensor 48 which produces pressure indicating analog signals which are converted to digital codes by an A/D converter 49 and passed therefrom to the microprocessor 32 for recording and use in automatic analyses.

Patient body temperature may be sensed by temperature sensor 19, such as a thermistor, which generates temperature proportional analog signals which are converted to representative digital codes by an A/D converter 50 and are passed to the microprocessor 32 for analysis and recording. Simiarly, the patients blood pressure may be sensed and data defining same recorded and used for analysis under control of microprocessor 32. For this purpose, blood pressure sensors 21 provide signals indicative of systolic and diastolic blood pressure which signals are converted to representative digital codes by an A/D converter 51 and passed to the microprocessor 32. The microprocessor 32 also provides on/off drive signals to an air pump 52, for controlling pump motor driver 53, wherein the pump delivers air pressure to the blood pressure cuff 20 via hose 22 for the inflation of the cuff. Alternatively, tonometric blood pressure measuring means may be employed.

Also included in system 10 are a body fluid analysis system 30, and a histological analysis system 29, both of which are interactive with the microprocessor 32 and provide digital data to the microprocessor 32 about their respective analyses for recording, comparison and analysis therein. A computer 27 is included which interacts with the microprocessor 32 via an I/O interface 54.

System 10 may be operated to request additional or more complete testing, or to generate additional patient data dependent upon the outcome of the present test analysis and comparisons of such present analysis with past analyses. The system 10 is also operable to alter its own programming according to programmed rules in order to obtain a proper diagnosis by the interaction of memories 33, 37, 31, 41 and 28 with the computer 27 and the operator of the system via the monitor 14, thus providing an automatic analysis by means of artificial intelligence. Select patient data, test analysis, specifics of test procedures, imaging or environmental data may be transferred to the archival memory storage means 28 as desired for later reference.

Figure 3:
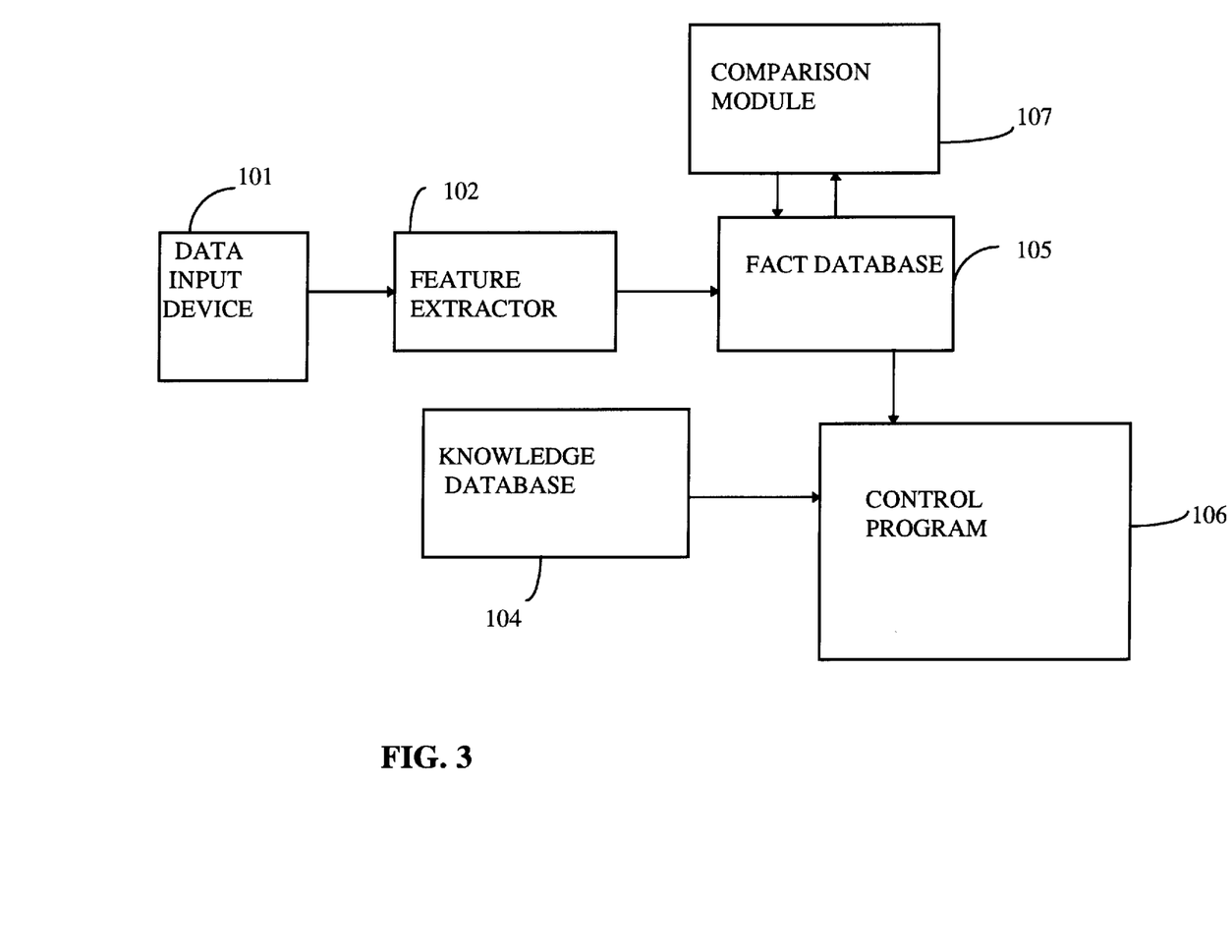
FIG. 3 is a block diagram of the information processing modules used to evaluate the clinical input data.

As set forth above, raw data inputs are provided for the system 10 by imaging and non-imaging sensors as well as by manually inputting other data such as codes defining variables relating to the patient's medical history or the results of a physical examination. Such raw data inputs are then analyzed by a number of information processing modules, as depicted in FIG. 3, which may consist either of dedicated hardware modules, separate program modules running on a single computer, or any combination thereof.

In analyzing image data, an image defined by analog video signals or the like of a selected anatomical region of the patient's body is converted to digitized form suitable for computer analysis. Depending on the patricular type of imaging modality employed, the digitizing step may be performed by the imaging apparatus itself. In employing computerized axial tomography (CAT), positron emission tomography (PET), and magnetic resonance imaging (MRI) scanners, for example, digitization is inherent in the image generation process, while a B-mode ultrasonic scanner or thermographic scanner may produce pixel intensity values in analog form which are digitized before further processing. Each image input to the system consists of an array of digital pixel intensity values which, when converted to analog gray scale values or color video signals, may be used to drive a CRT or the like and thus provide a visual display of the image.

A digitized image produced by any of the imaging modalities noted above is analyzed by the system as an array of pixel intensity values. The pixel intensity values are analyzed as such irrespective of whether they are used to display shades of black and white or different colors on a video monitor. By generating a series of cross-sectional two-dimensional images along a single longitudinal coordinate axis, a composite three-dimensional image may be obtained. In the description that follows, the term "image" includes three-dimensional as well as two-dimensional images. In order to generate a three-dimensional image, three location coordinates have to be assigned to each image pixel. Two of the coordinates define the location of the pixel in the cross-sectional plane of the two-dimensional image while the third location coordinate defines the location along the longitudinal axis.

The way in which location coordinates are assigned to each image pixel depends upon the particular imaging modality. For example, with a conventional CAT scanner, the x-ray tube emits a narrow beam of x-rays toward the patient with an x-ray detector, such as an array of scintillation detectors, positioned on the opposite side of the patient on which an x-ray shadow is formed. The x-ray tube and detectors, mounted on a rigid gantry, are rotated in multiple steps about the body until an entire axial slice is viewed from multiple angles. Codes defining the data acquired by the scintillation detectors are entered into a computer which uses mathematical algorithms to recontstruct a cross-sectional image of the region examined. The computerized scanner calculates the degree to which the tissue interposed between the x-ray tube and the detectors absorb the x-ray beam and thereby provides an attenuation coefficient for each area of tissue examined. Essentially, the quantity of x-ray absorbed in small volumes(voxels) of body tissue in the slice is computed. Computer analysis of the data collected then allows assignment of a numerical value to each small area (pixel) of the cross-sectional plane. By means of a digital-to-analog converter, the numerical value of each pixel is translated to a gray scale (or differential color scale) for driving a CRT display.

Due to the nature of the CAT scanning image reconstruction algorithm, the computer necessarily must assign location coordinates in the cross-sectional plane to each pixel with respect to the x-ray detector in order to generate the displayed image. Such coordinates are computed with respect to the patient support structure in the axial plane which is being imaged. In order to generate a three-dimensional image, another cooordinate along the longitudinal axis is needed. In order to assign a longitudinal location coordinate with respect to the patient support structure for each pixel, the positions of the x-ray tube and detector with respect to the patient support surface are sensed, and digital signals are generated which are input to the computer during the imaging procedure. The location coordinates for each pixel making up the image with respect to the patient support structure may be then readily calculated. A similar technique may be applied to PET scans.

In pulse-echo ultrasound techniques, an ultrasonic pulse is transmitted through the body tissues with the reflected echoes from each acoustical interface sensed by a transducer in order to provide a train of digital signals which define an image of the underlying structure. In so-called B-mode ultrasound, the pulse-echo procedure is performed in scanning fashion to image the underlying morphologic structures in a tomographic format. The resulting scanning signals, after digitization, can then be used by the computer to construct a two-dimensional array of pixel values for driving a display. Each pixel, in order to construct an image, is thus assigned a coordinate location with respect to the transducer in the same plane at which the ultrasound is emitted. Conventional ultrasonic scanning, however, requires that the ultrasonic transducer be contacted to the body surface over the region to be examined and positioned so as to scan at various angles. In order for the computer to compute the location coordinates for each pixel making up a display of an ultrasonic scan, the transducer is mounted on a movable arm having sensors in its joints for producing signals proportional to the degree of flexion of each such joint, which signals are then fed to the computer for calculation of the arm's position and orientation. Using appropriate scaling factors, the location coordinates for each pixel making up the image with respect to the patient support means may be readily calculated by a computer supplied with the above-mentioned data.

Computerized image construction in conventional MRI scanners, for employment in the present invention, is similar to that used in CAT scanners in that intensity values for an array of pixel values are computed with each pixel value stored in the computer assigned a set of location coordinates in order to generate the image. In MRI scanning, nuclei such as protons are subjected to a magnetic field gradient, called the slice-select gradient, which varies along the axis perpendicular to the plane of the image. Certain protons within the magnetic field gradient are excited to resonance by a so-called 90 degree RF pulse which causes them to emit detectable radiation. The amplitude and frequency of such emitted radiation is used to assign proton density values to pixels and generate the MRI image. The location coordinates of each pixel in the image are with respect to the patient support structure within the plane of the image cross-section, assuming the receiver coil of the MRI scanner remains at a fixed distance from the patient support structure. In order to derive a longitudinal coordinate value (ie., along an axis perpendicular to the plane of the cross-sectional image) for each pixel, it is necessary for the computer to compute the distance along the slice-select gradient with respect to the patient support structure where the Larmor frequency of the excited nuclei corresponds to the frequency of the 90 degree RF pulse. Such a computation only requires that the computer be supplied with data reflecting the magnitude of the slice-select gradient field versus distance and the frequency of the RF pulse which can either be assumed to be in accordance with computer command or can be sensed by magnetometers and a separate RF receiver coil. MRI scanners also allow the particular gradient fields to be generated along arbitrarily chosen axes so as to produce images not only in the transverse plane but also in coronal, sagittal, and oblique planes. The longitudinal coordinate for each image is then computed in the same way as just described along an axis perpendicular to the plane of the cross-sectional image. Finally, since the patient support structure and the MRI imaging apparatus are relatively moveable with respect to one another, the computer is fed with data produced by position sensing means so that the location coordinates can be translated so as to be with respect to the patient support structure.

The digitized image signals generated by an input device 101 (eg., any of the imaging modalites described above) are input to a feature extractor 102 which converts the image data into useful measurement data or codes. In order to extract such features, the image data signals are first subjected to a segmentation process which groups the pixels of the image into distinct entities representing separate organs, parts of organs, tumors, or other anatomical structures. Such segmentation may be accomplished by methods well-known to those of skill in the computer vision art such as: (1) edge-based approaches where intensity discontinuities are detected, and the pixels are then clustered into regions bounded by the detected edges, (2) textural segmentation approaches where the image is partitioned into non-overlapping regions based on textural homogeneity of groups of pixels which may involve, for example, either region growing by sequentially adding similar pixels to a local starting point, or region splitting where the entire image is sequentially divided into smaller regions on the basis of pixel intensity dissimilarity, or (3) matching approaches utilizing a standard image of the same anatomical region where the organs and anatomical structures of the standard image are used as templates for matching with analogous structures in the input image. A feature extractor in accordance with the present invention may make use of any or all of those methods as well as other pattern recognition methods such as neural networks. The feature extractor may also provide for user assisted segmentation where the image is displayed to an operator who then defines the relevant anatomical structures by means of, for example, a cursor or light pen in response to prompts from the system.

After the segmentation process, the feature extractor then processes the image data into information which is useable by the system in performing clinical diagnosis. Such information will typically include the size and shape of the segmented regions as well as the spatial distribution of a pattern of intensities over a particular region (ie., its texture). The resulting extracted features from the input image (hereinafter referred to as a feature vector) are next input into a clinical data interpreter 103 which evaluates the clinical significance of the features. In a preferred embodiment, the data interpreter is a rule-based artificial intelligence program of a type sometimes referred to as a production system or an expert system. The data interpreter comprises (1) a knowledge database 104 having a set of rules or productions which allow the generation of new information on the basis of currently known facts, (2) a fact database 105 of clinical facts which includes image feature vectors, and (3) a control program 106 (such as an inference engine) operable for determining the applicability of the rules in the context of the current database, the selection of appropriate rules, and operating on the fact database by means of the selected rules.

In accordance with the present invention, the fact database 105 comprises feature vectors from input images as well as other clinical parameters input into the system which are determined by other means, such as physical examination or laboratory tests as well as the patient's medical history. In a particular embodiment, the fact database may also contain comparison codes generated by comparison module 107 which represent the differences between a presently input feature vector and a stored feature vector extracted from a previous image of the same anatomical region of the same patient. Such comparison codes represent changes in the patient's condition as reflected by present and past images. Comparison codes may also be used to represent the difference between the patient's image and a standard image of the same anatomical region, features extracted from the latter also being stored in the fact database 105.

The knowledge database 104 contains the logic used by the system in evaluating the clinical significance of the feature vector. Each rule of the knowledge database is typically in the form of an implication or IF-THEN statement. Each such rule thus has a premise and a conclusion where the premise may consist of any number of clauses representing factual statements or conclusions which are combined disjunctively or conjunctively. When the premise is satisfied, the rule is "fired," and the rule's conclusion is taken by the system to be true. That conclusion may then be used by the system in activating other rules and so on. The rules thus represent the relationships between clinical parameters such as image features and clinical conclusions based on current medical knowledge. The ultimate clinical conclusions contained in the rules are typically explicit statements reflecting an assessment of the patient's condition. Such statements may include, for example, "the size of the tumor has increased," "the abscess has disappeared," or "lung consolidation indicates pneumonia." Using what is referred to as forward-chaining, database facts and/or conclusions from applicable rules are linked to the premises of other rules until one or more ultimate clinical conclusions are reached. In the event that no such ultimate conclusion can be verified, the system outputs the premises needed for such a conclusion in the form of a recommendation for further tests or data. Alternatively, if the system is capable of doing so, the additional test may be performed automatically.

The system may also perform backward-chaining of rules in order to test hypotheses about the patient's condition. In backward-chaining, conclusions are linked to premises containing factual statements, the latter being compared with the fact database. The chaining process is continued until premises are identified which, according to the fact database, establish the conclusion as true. If a premise is identified which, if true, would establish the conclusion, but there is currently no such information in the fact database about that premise, the system asks the user for the needed information in the form of a recommendation for further testing. The hypotheses to be tested may be generated automatically by the system as the product of rules or may be inputted manually by a system user.

Figure 4:
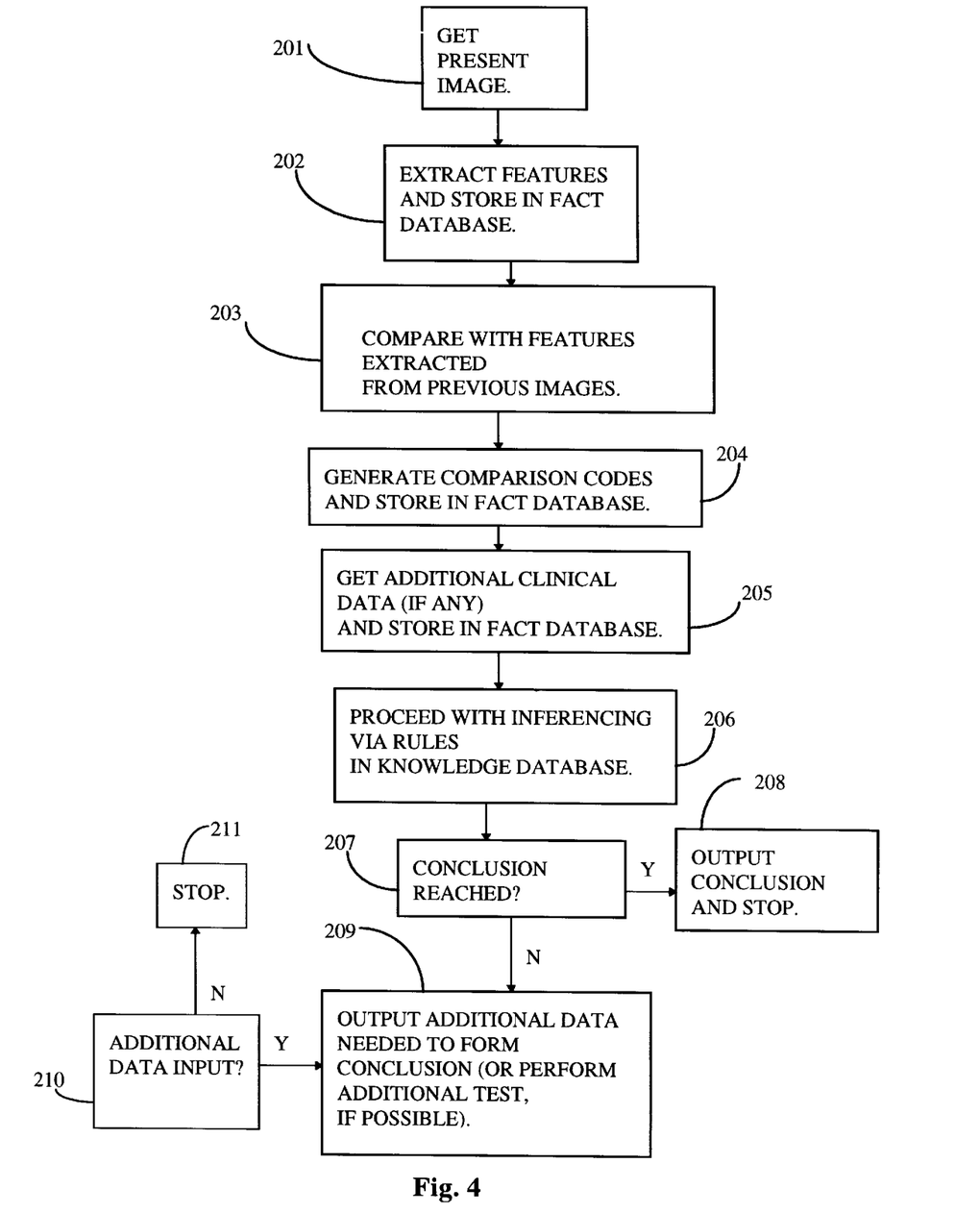
FIG. 4 is a flow diagram showing the basic steps performed by a system in accordance with the present invention.

FIG. 4 is a flow diagram illustrating the basic method of analysis as described above. A present image is generated at step 201, and features from the image are extracted and stored in the fact database at step 202. The features extracted from the present image are compared with features extracted from previous images (or from a standard image) at step 203, and comparison codes are generated and stored in the fact database at step 204. Additional clinical data, either input manually by the system operator or input from other automatic testing modalities as described below, is stored in the fact database at step 205. The data contained in the fact database is then evaluated at step 206 using the rules contained in the knowledge database. If a conclusion can be reached at step 207, that conclusion is output at step 208. If no such conclusion can be reached, the additional data needed to form a conclusion (generated at step 206) is output at step 209 or, if the system has the capability, the test generating the needed data is automatically performed. Whether or not the additional needed data has been input to the system is tested at step 210. The system then either returns to step 205 or terminates at step 211.

The method of data analysis described above is that of a rule-based artificial intelligence system. Alternative embodiments of the present invention may make use of fuzzy logic rules operating on clinical data coded according to its degree of membership in fuzzy sets. Such fuzzy logic rules may be used both in feature extraction and as part of the knowledge database 104 used to generate clinical conclusions. It is contemplated that the fuzzy logic rules and membership functions to be used would be generated by experienced clinicians or as a result of training a neural network adapted for generating such rules.

The system may also incorporate non-imaging diagnostic testing modalites such as blood pressure and heart rate monitoring or EKG monitoring. Sensor generated analog signal data from such tests is digitized, processed, and then input from input device 101 to a rule-based feature extractor 102 to produce feature vectors which are input into the fact database 105 similar to the image feature vectors described above. Feature vectors generated from each test are stored for later use in generating comparison codes as described above with respect to the interpretation of image data. In one embodiment of the invention, the particular tests performed by the system may be selected automatically by the clinical data interpreter 103 where certain clinical conclusions take the form of commands to perform a certain test. For example, a rule might say that if cardiac enlargement is detected from the image data, then a system command is to be generated which results in an EKG being performed.

The system may also incorporate means for automatically performing a sequence of laboratory tests upon samples of a patient's tissue, blood, urine, or other bodily fluid. In such a system, the results of each test performed are output in the form of electrical signals which are digitized and input from input device 101 to a feature extractor 102 similar to that described above with respect to image processing. A feature extractor for non-image data is usually quite simpler than for image data since, in many cases, the amplitude of the signal (ie., the laboratory value, such as hematocrit, blood gas measurement, serum glucose, etc.) is all that is of interest. A comparison code may then be generated by comparing the resultant value of the test with standard norms and/or results of past tests on the same patient. The values of each test performed as well as any comparison codes are then stored in the fact database 105. Using production rules similar to those described above, the data interpreter 103 may then generate diagnostic conclusions and/or recommendations for further testing. In addition, the data interpreter may generate commands which instruct the system to perform particular tests in an optimum sequence based on the information in the fact and rule databases. The results of each test are entered into the fact database 105 as soon as the test is performed and analyzed, allowing the data interpreter 103 to select the next test to be performed based on facts which include the result of the last test. One particular advantage of the present invention as applied to automated laboratory testing accrues due to the cost of each particular test performed. By employing the data interpreter to select the sequence of tests to be performed, the sequence of tests may be optimized so as to eliminate unnecessary testing.

What is claimed is:

1. A method for diagnosing and evaluating disease in a patient, comprising the steps of:

generating a present image of a selected anatomical region of the patient's body and inputting digital signals corresponding to said image into a computer;

extracting features relating to particular disease states from said image signals with a pattern recognition program and storing feature signals corresponding to said extracted features in a fact database accessible by said computer;

comparing said extracted feature signals with similar feature signals corresponding to features extracted from a second image of the same anatomical region which is stored in said fact database, producing a comparison code relating to each such comparison, and storing said comparison codes in said fact database;

operating on a plurality of production rules contained in a rule database stored within said computer and relating said comparison codes to certain disease states by an inference program to generate and intelligibly indicate a diagnostic assessment of the patient's condition based on differences between the present and second images.

2. The method as set forth in claim 1 wherein said inference program forward-chains production rules in order to generate said diagnostic assessment.

3. The method as set forth in claim 1 wherein said second image is a previously generated image of the patient's body, and said comparison codes represent changes in the patient's condition over time.

4. The method as set forth in claim 1 wherein said second image is a standard image of the anatomical region being examined.

5. The method as set forth in claim 1 wherein said diagnostic assessment includes intelligible recommendations for further diagnostic tests.

6. The method as set forth in claim 1 wherein said extracted features include sizes of regions segmented from an input image.

7. The method as set forth in claim 1 wherein said extracted features include shapes of select regions of an image field segmented from the input image.

8. The method as set forth in claim 1 wherein said extracted features include textures of regions segmented from an input image.

9. The method as set forth in claim 1 wherein said inference program operates on said production rules by backward-chaining a plurality of production rules in order to test a hypothetical assessment of the patient's condition.

10. The method as set forth in claim 1 wherein said fact database includes signal recordings defining non-image features representing clinical parameters and further wherein said production rules relate said non-image features to particular disease states.

11. The method as set forth in claim 10 further comprising the step of automatically performing a diagnostic test in response to a command generated by the inference program.

12. A system for diagnosing and evaluating disease in a patient comprising:

an imaging apparatus for generating signals defining a digitized first image of a selected anatomical region of the patient's body and inputting said image signals into a computer;

means for extracting features relating to particular disease states from said image signals with a pattern recognition program and storing the extracted features in a fact database;

wherein said fact database further includes a digitized second image of the same anatomical region as the first image;

means for comparing signals defining said extracted features with signals defining similar features extracted from a second image of the same anatomical region which are stored in said fact database, producing a comparison code relating to each such comparison, and storing said comparison codes in said fact database;

means for generating inferences by operating on a plurality of production rules relating comparison codes to certain disease states in order to generate a diagnostic assessment of the patient's condition based on differences detected between the present and standard images.

13. The system as set forth in claim 12 wherein said inference generating means is operable to forward-chain production rules in order to generate said diagnostic assessment.

14. The system as set forth in claim 12 wherein said second image is a previously generated image of the patient's body, said comparison codes representing changes in the patient's condition over time.

15. The system as set forth in claim 12 wherein said second image defines a standard image of the anatomical region being examined.

16. The system as set forth in claim 12 wherein said diagnostic assessment includes recommendations for further diagnostic tests.

17. The system as set forth in claim 12 wherein said means for extracting features operates to extract features including the size of regions segmented from the input image.

18. The system as set forth in claim 12 wherein said means for extracting features operates to extract features including the shape of regions segmented from the input image.

19. The system as set forth in claim 12 wherein said means for extracting features operates to extract features including the texture of regions segmented from the input image.

20. The system as set forth in claim 12 wherein said inference generating means operates on said production rules by backward-chaining a plurality of production rules in order to test a hypothetical assessment of the patient's condition.

21. The system as set forth in claim 12 wherein said fact database contains information defining non-image data representing clinical parameters and further wherein said production rules relate said non-image data to particular disease states.

22. The system as set forth in claim 12 further comprising:

an input device for generating digitized non-image data from a diagnostic testing device under the control of said computer;

a non-image feature extractor for extracting features relating to particular disease states from said non-image data and storing the extracted features in said fact database;

wherein said comparison module is operable to compare extracted features with similar features extracted from non-image data previously stored in said fact database, produces a comparison code relating to each such comparison, and stores said comparison codes in said fact database; and, wherein said inference program operates on a plurality of production rules relating comparison codes to certain disease states to generate a diagnostic assessment of the patient's condition based on said comparison codes.

23. The system as set forth in claim 22 wherein a diagnostic test is automatically performed in response to a command generated by said inference program.

* * * * *

UNITED STATES PATENT AND TRADEMARK OFFICE
CERTIFICATE OF CORRECTION

PATENT NO. : 5,878,746
DATED : March 9, 1999
INVENTOR(S) : Jerome H. Lemelson, J. Kevin Parker It is certified that error appears in the above-identified patent and that said Letters Patent is hereby corrected as shown below:

Title page,
Between items [21] and [51], add a section titled -- Related U.S. Application Data --. Insert text on the next line: -- Continuation-in-part of application No. 08/111,837, filed August 25, 1993, now abandoned. --

Column 1,
After the title insert a section titled -- CROSS REFERENCE TO RELATED APPLICATIONS --. Insert text on the next line: -- This application is a Continuation-in-part of U.S. Patent application Serial No. 08/111,837, filed August 25, 1993, now abandoned. --

Signed and Sealed this

Sixth Day of November, 2001

*Attest:*

*Attesting Officer*

NICHOLAS P. GODICI
*Acting Director of the United States Patent and Trademark Office*